United States Patent [19]

Patil

[11] Patent Number: 4,592,352
[45] Date of Patent: Jun. 3, 1986

[54] COMPUTER-ASSISTED TOMOGRAPHY STEREOTACTIC SYSTEM

[76] Inventor: Arun A. Patil, 1011 Valley View Dr., Minot, N. Dak. 58701

[21] Appl. No.: 677,080

[22] Filed: Nov. 30, 1984

[51] Int. Cl.⁴ .............................................. A61B 17/00
[52] U.S. Cl. .................................. 128/303 B; 128/630
[58] Field of Search ................... 128/303 B, 660, 630; 250/445, 476

[56] References Cited

U.S. PATENT DOCUMENTS

| | | | |
|---|---|---|---|
| 1,129,333 | 2/1915 | Clarke | 128/303 B |
| 3,061,936 | 11/1962 | Dobbeleer | 128/303 B |
| 3,115,140 | 12/1963 | Volkman | 128/303 B |
| 3,223,087 | 12/1965 | Vladyka . | |
| 3,318,010 | 5/1967 | Mahl . | |
| 3,357,431 | 12/1967 | Newell . | |
| 3,457,922 | 7/1969 | Ray . | |
| 4,058,114 | 11/1977 | Soldner . | |
| 4,132,900 | 1/1979 | Smith . | |
| 4,139,776 | 2/1979 | Hellstrom . | |
| 4,341,220 | 7/1982 | Perry . | |
| 4,360,028 | 11/1982 | Barbier . | |
| 4,426,726 | 1/1984 | Cheetham . | |
| 4,463,758 | 8/1984 | Patil et al. | 128/630 |

FOREIGN PATENT DOCUMENTS

| | | | |
|---|---|---|---|
| 818711 | 8/1959 | United Kingdom | 128/303 B |
| 197706 | 6/1977 | U.S.S.R. | 128/303 B |

*Primary Examiner*—Stephen C. Pellegrino
*Assistant Examiner*—Gene B. Kartchner
*Attorney, Agent, or Firm*—Zarley, McKee, Thomte, Voorhees & Sease

[57] ABSTRACT

An apparatus is described for performing surgical procedures through a patient's skull to a target within the skull by utilizing a computer-assisted tomography scanner comprising a base platform which is positioned on the table of the scanner. A pair of vertically disposed support members are selectively longitudinally movably mounted at opposite sides of the platform and have arc carrier supports selectively vertically movably mounted thereon. An arc carrier is selectively pivotally mounted to the arc carrier supports and has an arcuate segment movably mounted thereon. A probe holder is selectively movably mounted on the arc.

12 Claims, 4 Drawing Figures

COMPUTER-ASSISTED TOMOGRAPHY STEREOTACTIC SYSTEM

BACKGROUND OF THE INVENTION

The technique of computerized or computer-assisted tomography was developed in approximately 1972 and involves a diagnostic X-ray system designed for neuroradiological investigation. Different techniques and instrumentations have been provided for computer-assisted tomography to accurately probe deep-seated brain lesions. In some instances, the CT scan is used for guidance and in other instances, the CT scan is combined with stereotactic techniques. In applicant's U.S. Pat. No. 4,463,758, a stereotactic frame is disclosed.

Generally in the stereotactic technique, calculations of three coordinates are required: namely, the X coordinate (the lateral), the Y coordinate (posterior-anterior distance) and the Z coordinate (the vertical heights from the reference baseline). In the stereotactic system described herein, the probe holder and the axis of rotation of the arc are placed in the same CT plane as the target using the laser positioning light thereby eliminating the need to calculate the Z coordinate (the distance from the baseline of scanning to the target). In addition, the utilization of the invention described herein enables one to directly measure the X and Y coordinates from a single picture without the need for special computer programming, calculations or special atlases.

It is therefore a principal object of the invention to provide an improved stereotactic system.

A further object of the invention is to provide an apparatus for performing surgical procedures through a patient's skull to a target within the skull by utilizing a computer-assisted tomography scanner.

Yet another object of the invention is to provide an apparatus of the type described which utilizes a planar approach to CT stereotaxis which enables the measurement of the coordinate to be done in one plane which is in the same vertical plane of the CT picture in which the target is located.

Still another object of the invention is to provide an apparatus of the type described wherein the center of the probe holder and the circular attachment are aligned in the same plane which enables the two elements to be aligned in the same CT plane as the target utilizing the vertical positioning light of the CT scanner.

Still another object of the invention is to provide an apparatus of the type described wherein targets within the skull can be approached from the lateral position.

Still another object of the invention is to provide an apparatus of the type described including a movable head holder mounted thereon to enable the head holder to be selectively moved to a position out of the plane of the CT scanner to eliminate any possibility of artifact.

Still another object of the invention is to provide a system which utilizes the top surface of the base platform and the central marker on the base platform as reference markers so that the apparatus may be used with any CT scanner.

Still another object of the invention is to provide an apparatus which is compatible with nuclear magnetic resonance scanners.

Yet another object of the invention is to provide an apparatus which may be easily removed from the table of the CT scanner.

These and other objects will be apparent to those skilled in the art.

SUMMARY OF THE INVENTION

The apparatus of this invention enables surgical procedures to be performed through a patient's skull to a target within the skull by utilizing a computer-assisted tomography scanner. The apparatus includes a base platform which is removably mounted on the top surface of the table of the scanner. The base platform has opposite sides and first and second ends with the opposite sides having indicia thereon. One of the ends of the base platform has a center marker provided therein. Vertically disposed support members are selectively longitudinally movably mounted at each of the opposite sides of the platform and are also provided with positioning indicia thereon. Arc carrier supports are vertically movably mounted on the support members and have the lower ends of an arc carrier pivotally mounted thereon. An arcuate arc is laterally movably mounted on the upper end of the arc carrier and has a probe holder movably mounted thereon.

DESCRIPTION OF THE PREFERRED EMBODIMENT

Figure 1:
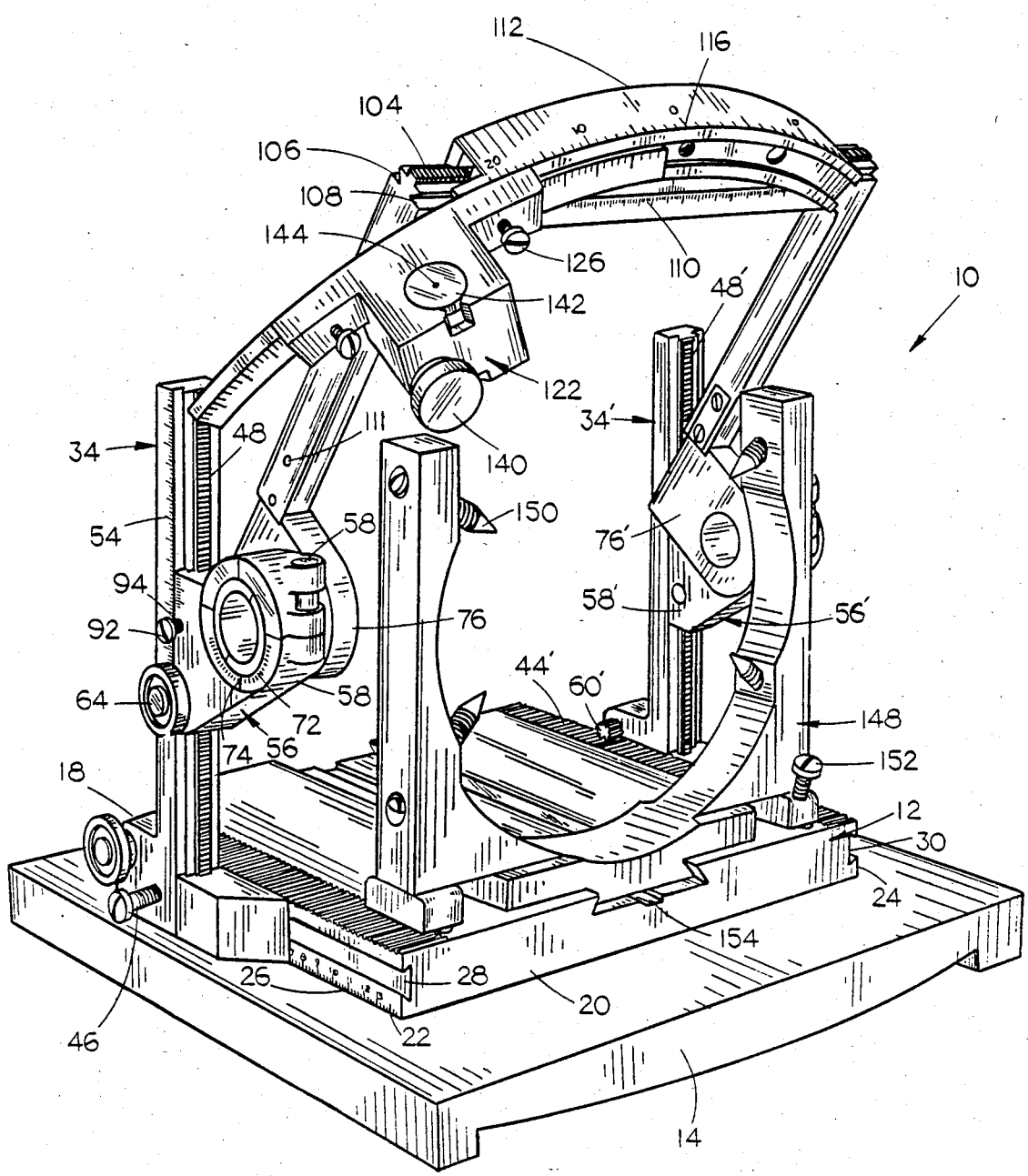
FIG. 1 is a perspective view of the apparatus of this invention.
Figure 2:
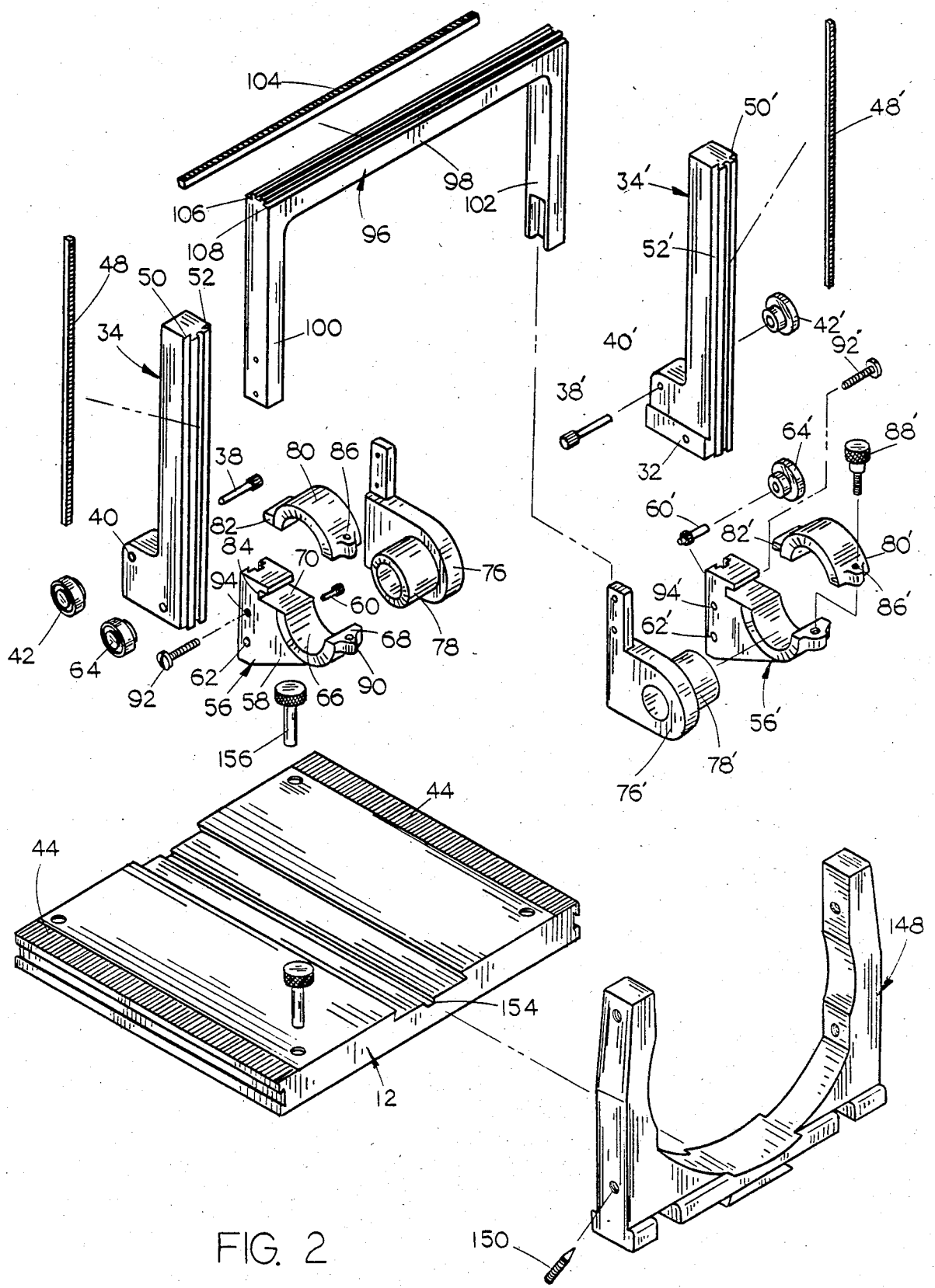
FIG. 2 is a partial exploded perspective view of the apparatus of this invention.
Figure 4:
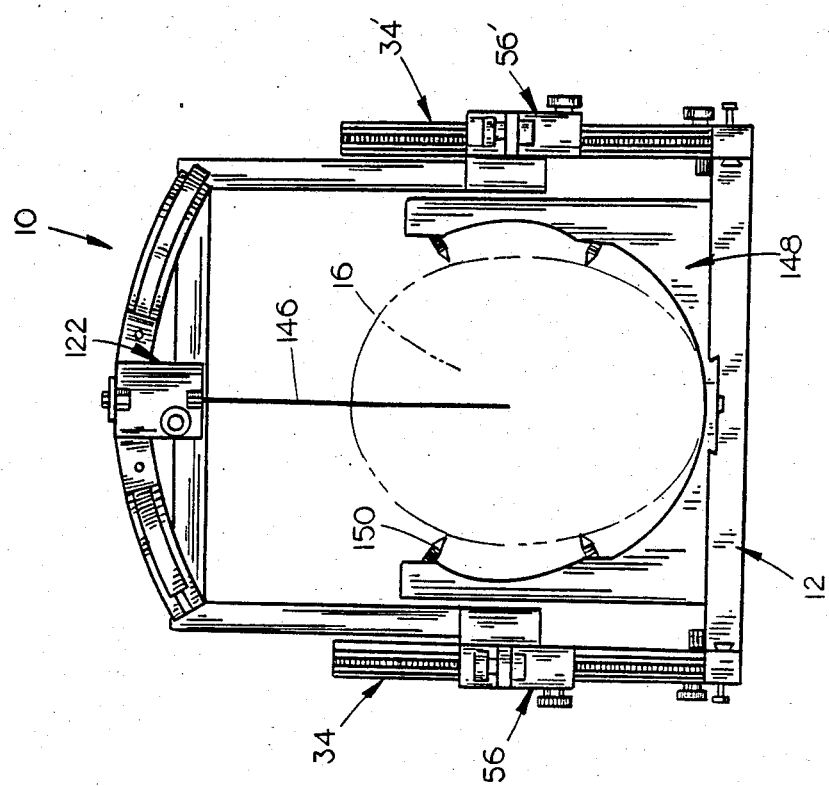
FIG. 4 is an end view of the apparatus with the broken lines indicating a patient's head.

The apparatus or system of this invention is referred to generally by the reference numeral 10 and generally includes a base platform 12 which is mounted on an attachment 14 which is designed to be removably mounted or positioned on the top surface of the table of the CT scanner. For purposes of illustration, the numeral 16 refers to a patient's skull. Platform 12 includes opposite ends 18, 20 and opposite sides 22 and 24. The sides 22 and 24 are provided with positioning indicia 26 provided thereon. Each of the sides 22 and 24 are provided with grooves 28 and 30 formed therein which slidably receive tongues 32 which extend inwardly from the lower ends of support members 34 and 36. Pinion 38 is rotatably mounted in bore 40 of support member 34 and has thumb wheel 42 mounted on the outer end thereof. The inner end of pinion 38 is in engagement with the rack 44. Screw 46 threadably extends inwardly through the lower end of support member 34 for engagement with the side of the base platform to positively maintain the support member 18 in position relative to the side of the base platform as desired. As seen in the drawings, one side of the support member 34 is provided with a rack 48 positioned between groves 50 and 52. Positioning indicia is provided on the lateral side of support member 34 as seen in FIG. 1.

Support member 34' is also provided with a bore 40' formed therein in which is rotatably mounted the pinion 38', the inner end of which is in engagement with the rack 44'. Thumb wheel 42' is provided on the outer end of the pinion 38' for rotating the same. As seen in the drawings, support member 34' is also provided with rack 48 which is positioned between the grooves 50' and 52'. Support member 34' is provided with indicia on the side thereof which corresponds with the indicia 54.

Arc carrier supports 56 and 56' are selectively vertically movably mounted on the support 34 and 34' respectively. Inasmuch as the arc carrier supports 56 and 56' are identical, only arc carrier support 56 will be described in detail with "'" indicating identical structure on arc carrier support 56'.

Arc carrier support 56 includes a lower portion or circular attachment 58 which is vertically movably mounted on the support member 34 as indicated in the drawings. Pinion 68 is rotatably mounted in bore 62 and is in engagement with the rack 48 whereby movement of the thumb wheel 64 mounted on the pinion 60 will cause rotation of the pinion 60 and vertical movement of the lower portion 58 relative to the support member 34. Lower portion 58 includes a semi-circular shaped portion 66 terminating in shoulder portions 68 and 70. The lateral side of lower portion 58 is provided with positioning indicia referred to generally by the reference numeral 72 and including a vertical indicia 74 which indicates the center of the recessed portion 66 which coincides with the central axis of rotation of the upper portion 76 of arc carrier support 56 which is pivotally or rotatably mounted in the recessed portion 66. Upper portion 76 of arc carrier support 56 includes a cylindrical portion 78 extending outwardly therefrom which is received by the recessed portion 66 and which is held therein by means of the cap portion 80. Cap portion 80 includes a lip 82 which is removably received by the groove 84 and an opening 86 adapted to receive the cap screw 88. The lower threaded end of cap screw 88 is adapted to be received by the threaded opening 90 in lower portion 58. Screw 92 extends inwardly through opening 94 in lower portion 58 for engagement with the support member 34 to aid in positively maintaining the arc carrier support in position relative to the support member 34 as desired or required.

The numeral 96 refers to an arc carrier comprised of top portion 98 and legs 100 and 102 extending downwardly therefrom at opposite ends thereof. Top portion 98 has a rack segment 104 mounted thereon between grooves 106 and 108. One side of top portion 96 is provided with positioning indicia 110 as illustrated in FIG. 1. The lower ends of legs 100 and 102 are secured to the upper portions 76 and 76' respectively by screws 111. As seen in the drawings, the legs 100 and 102 are secured to the upper portions 76 and 76' between the axis of pivotal rotation between the upper and lower portions of the arc carrier support and the support members 34 and 34'.

Figure 3:
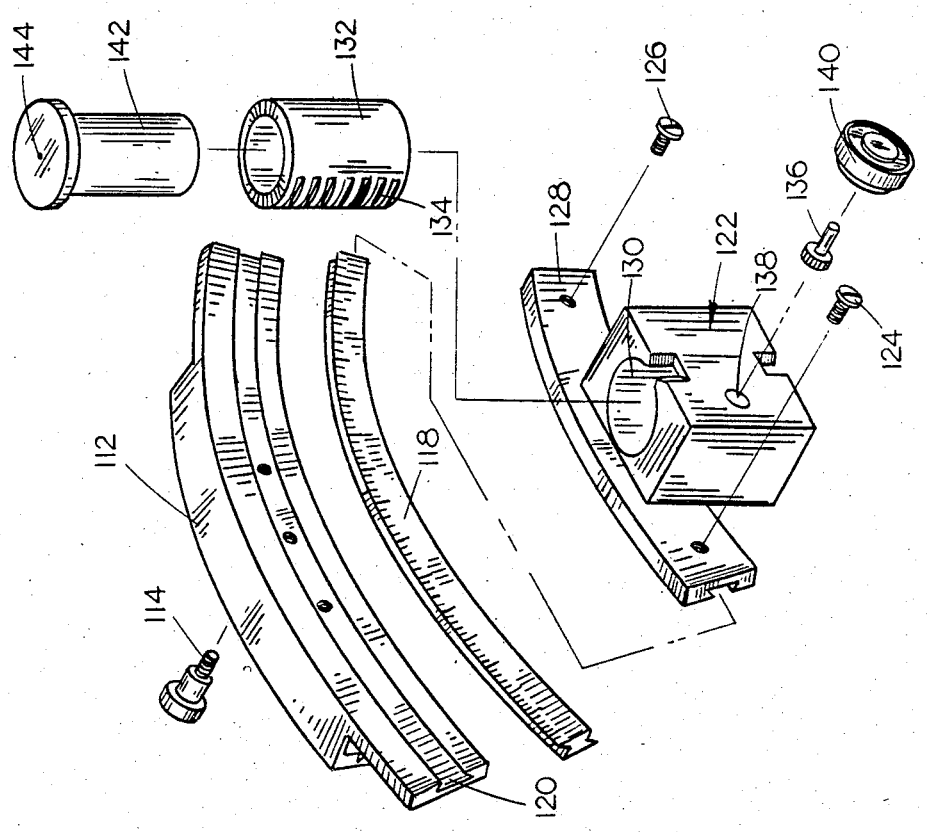
FIG. 3 is a partial exploded perspective view of the probe holder and arc.

Arcuate segment 112 is movably mounted on the arc carrier 96 as indicated to the drawings. Pinion 114 rotatably extends into the backside of the arc 112 and is in engagement with the rack segment 104 whereby rotation of the pinion 114 will cause the arc 112 to be laterally moved relative to the arc carrier. Arc 112 is provided with indicia 116 on its upper surface which depicts angular displacement either side from "0". Support 118 is selectively movably mounted in groove 120 in arc 112 and has probe holder 112 selectively movably mounted thereon as illustrated in FIG. 3. Screws 124 and 126 threadably extend inwardly through support portion 128 of probe holder 122 for engagement with the member 118 to positively maintain the probe holder 122 in position relative to member 118 as desired or required. Probe holder 122 is provided with a cylindrical bore 130 extending downwardly therethrough which receives the collar 132 having vertically spaced-apart notches 134 formed at one side thereof. Pinion 136 is mounted in opening 138 of probe holder 122 for engagement with the notches 134 whereby rotation of the thumb wheel 140 will cause the collar 132 to be raised or lowered relative to the probe holder. Probe holder cylinder 142 is mounted in the collar 132 and has an elongated bore 144 formed therein adapted to receive the probe 146. Bore 144 is laterally offset from the arc 112 such that when the arc holder is perfectly vertically disposed, the axis of the bore 144, and thus the probe 146, will intersect the axis of rotation between the upper and lower portions of the arc carrier supports. Accordingly, in all positions of angular displacement of the arc carrier support, the axis of the bore 144 will dwell in the same plane as the axis of rotation between the upper and lower positions of the arc carrier supports.

The numeral 148 refers to a head holder which is selectively longitudinally movably mounted on the base platform 12 as illustrated in FIG. 1. Head holder 148 includes screws 150 extending inwardly therefrom for engagement with the patient's head. Screw 152 extends inwardly through the lower end of the head holder 148 for engagement with the base platform to positively maintain the head holder 148 in position relative to the base platform 12 as required. As seen in FIG. 1, base platform 12 is provided with a center marker 154 which will be visible in the CT scan to enable desired measurements to be taken as will be described in more detail hereinafter.

In operation, the base platform 12 may be secured to the member 14 by means of screws 156. The attachment 14 may then be placed on the top surface of the CT scan table. Normally, the arc carrier is initially removed from the apparatus by removing the screws 58 and 58' so that the cap portions 80 and 80' may be removed from the lower portions 58 and 58'. The arc carrier 96 and the upper portion 76 and 76' are then removed from the arc carrier supports 56 and 56'. With the base platform perfectly parallel to the length of the CT table, the patient's head is positioned in the head holder and CT pictures are taken in the region of the target. If the head holder 148 is visible in the CT image in which the target is localized, the head holder 148 is moved to another position to avoid artifact. The pins 150 are then secured to the patient's head and another picture is taken in the CT plane of the target. The laser positioning light of the CT scanner is then illuminated, and the support members 34 and 34' are then moved along the length of the platform until the lower portions 58 and 58' of the arc carrier supports are so positioned so that the laser positioning light coincides with the vertical line 74. The X and Y coordinates are then measured from a single CT picture on which the target is localized. Using the cursor of the scanner, the perpendicular distance from the center marker 154 to the target is measured as the X coordinate and the distance from the top surface of the base platform to the target is measured as the Y coordinate. Adjustment of the Y coordinate is done by moving the arc carrier supports 56 and 56' to the required height. Adjustment of the X coordinate is done by moving the middle of the arc to the distance equal to the X coordinate. After these adjustments are made, the arc carrier 96 is repositioned on the arc carrier supports 56 and 56'. The arc carrier 96 may then be moved to any desired angle and the probe holder 122 on the arc 96 may be rotated to any desired angle so as to reach the target through any point on the skull.

The burr hole can be placed before the patient is brought to the CT scan room, at any suitable point that is felt to be safe and as close as possible to the target. Alternately, a twist drill hole may be placed in the CT room. Or after measurements are taken, the patient can then be moved together with the system in one piece to the operating room and the burr hole placed and the target approached in the operating room. During biopsy, the probe can be moved to different depths to obtain tumor specimens at different depths.

It can therefore be seen that the apparatus of this invention does achieve all of the stated objectives since the surgical procedures may be performed without any calculations or special computer programming being required. The apparatus of this invention is free of artifact. Further, the apparatus of this invention permits laterally placed targets to be reached with ease. In applicant's invention, there is no need for calculating or measuring the Z coordinate and there is no need for intermediate frame or simulator for calculating coordinates. The apparatus of this invention can be used before, during or after CT imaging. The apparatus disclosed herein is NMR compatible and is compatible with any type of body scanner. It can therefore be seen that the system of this invention accomplishes at least all of its stated objectives.

I claim:

1. An apparatus for performing surgical procedures through a patient's skull to a target within the skull by utilizing a computer-assisted tomography scanner (hereinafter "CT scanner") comprising, a base platform of material registerable on the CT scanner and having opposite sides and first and second ends, means for removably mounting said base platform on the table of the scanner, a vertically disposed support member selectively longitudinally movably mounted at each of said opposite sides of said platform, said sides of said base platform having positioning indicia thereon for indicating the longitudinal positioning of said support members relative to said base platform, an arc carrier support selectively vertically movably mounted on each of said support members, an arc carrier selectively pivotally mounted on said arc carrier supports and extending upwardly therefrom, said arc carrier comprising first and second spaced-apart legs having upper and lower ends and a top portion extending between the upper ends thereof, the lower ends of said legs being operatively pivotally secured to said arc carrier supports, an arcuate arc selectively movably mounted on said top portion of said arc carrier for movement parallel to the pivotal axis of said legs, said arc having a radius greater than one-half the distance between said legs, a probe holder assembly selectively movably mounted on said arc, said probe holder assembly having a cylindrical bore provided therein for receiving an elongated probe or the like, the pivotal connection between said legs and said arc carrier supports being longitudinally offset from said support members towards said one end of said base platform, said legs being longitudinally offset from said pivotal connection, at least one of said arc carrier supports having vertical indicia thereon for indicating the pivotal axis of said pivotal connection, said cylindrical bore in said probe holder assembly being positioned so that its longitudinal axis intersects the central axis of said pivotal connection between said legs and said arc carrier supports, said base platform having a longitudinal groove centered therein, said groove registerable on the CT scanner and indicative of the lateral center of said platform, and a head holder assembly selectively longitudinally movably mounted on said base platform.

2. The apparatus of claim 1 wherein said support members have indicia appearing on the sides thereof for aid in positioning said arc carrier supports.

3. The apparatus of claim 1 wherein said arc carrier is removably mounted on said arc carrier supports.

4. The apparatus of claim 1 wherein said top portion of said arc carrier has indicia appearing thereon for aid in positioning said arcuate arc relative thereto.

5. The apparatus of claim 4 wherein said arc has indicia appearing thereon for aid in positioning said probe holder assembly relative thereto.

6. The apparatus of claim 1 wherein said arc carrier supports are movably mounted on said support members by a rack and pinion system.

7. The apparatus of claim 1 wherein said support members are movably mounted on said base platform by a rack and pinion system.

8. The apparatus of claim 1 wherein said arc is movably mounted on said top portion by a rack and pinion system.

9. The apparatus of claim 1 wherein said arcuate arc includes first and second arc portions slidably connected together, said first arc portion mounted on said top portion of said arc carrier and said second arc portion having said probe holder assembly mounted thereon, said second arc portion adapted to project beyond an end of said first arc portion when selectively slided therealong, and adapted to extend the slidable range of said probe assembly in relation to said first arc portion.

10. The apparatus of claim 9, wherein said first arc portion of said arc has indicia occurring thereon for aid in positioning said probe holder assembly on said second arc portion relative thereto.

11. The apparatus of claim 10, wherein said second arc portion has indicia occurring thereon for aid in positioning said probe holder assembly relative thereto.

12. The apparatus of claim 1, wherein said head holder assembly is oriented in the vertical plane, generally parallel to the scanning plane of the CT scanner.

* * * * *